(12) United States Patent
Lynch et al.

(10) Patent No.: US 7,685,861 B2
(45) Date of Patent: Mar. 30, 2010

(54) METHOD AND APPARATUS FOR CALIBRATING AN ULTRASONIC SENSING SYSTEM USED TO DETECT MOVING OBJECTS

(75) Inventors: John Edward Lynch, Williamsburg, VA (US); David Mark Blaker, Roanoke, VA (US); Ronald E. Hileman, Durham, NC (US)

(73) Assignee: Luna InnovationsIncorporated, Roanoke, VA (US)

( * ) Notice: Subject to any disclaimer, the term of this patent is extended or adjusted under 35 U.S.C. 154(b) by 567 days.

(21) Appl. No.: 11/651,105

(22) Filed: Jan. 9, 2007

(65) Prior Publication Data

US 2008/0092623 A1 Apr. 24, 2008

Related U.S. Application Data

(60) Provisional application No. 60/852,431, filed on Oct. 18, 2006.

(51) Int. Cl.
*G01M 1/14* (2006.01)
(52) U.S. Cl. ...................................... 73/1.86
(58) Field of Classification Search ............... 73/1.86
See application file for complete search history.

(56) References Cited

U.S. PATENT DOCUMENTS

| | | | | |
|---|---|---|---|---|
| 3,791,192 | A | * | 2/1974 | Butler .......................... 73/1.03 |
| 5,184,510 | A | * | 2/1993 | Rossman .................. 73/290 V |
| 5,230,339 | A | | 7/1993 | Charlebois |
| 5,433,112 | A | * | 7/1995 | Piche et al. ..................... 73/597 |
| 5,441,051 | A | | 8/1995 | Hileman et al. |
| 5,463,906 | A | | 11/1995 | Spani et al. |
| 5,902,748 | A | | 5/1999 | Madsen et al. |
| 6,083,159 | A | | 7/2000 | Driscoll et al. |
| 6,148,655 | A | | 11/2000 | Hall et al. |
| 6,295,873 | B1 | | 10/2001 | Condreva |
| 6,517,484 | B1 | | 2/2003 | Wilk et al. |
| 2003/0051535 | A1 | | 3/2003 | Coupland et al. |
| 2005/0020918 | A1 | | 1/2005 | Wilk et al. |
| 2005/0217346 | A1 | | 10/2005 | Nagarkatti et al. |
| 2006/0178581 | A1 | | 8/2006 | Africk et al. |

OTHER PUBLICATIONS

Related U.S. Appl. No. 11/429,432, filed May 8, 2006, Lynch et al.
510(k) Summary, IBC CM02 Flow Through Cuvette, Mar. 20, 2007, p. 28.
IBC Web page, IBC Products > CM02, Admitted Art.
BCC 200, *The Bubble Counter for Clinical Monitoring*, New System for Micro Bubble Detection, Admitted Art.
International Search Report and Written Opinion mailed Nov. 3, 2008 in corresponding PCT Application PCT/US07/00304.

* cited by examiner

*Primary Examiner*—Robert R Raevis
(74) *Attorney, Agent, or Firm*—Nixon & Vanderhye P.C.

(57) ABSTRACT

A calibration device is described for use in calibrating an ultrasonic pulse echo apparatus for detecting a moving object in a fluid, where the ultrasonic pulse echo apparatus includes an ultrasonic transducer and calibration circuitry. A connector has a first end for connecting with a first fluid conduit and a second end for connecting with a second fluid conduit. A cavity between the first and second ends permits the fluid containing the moving object from the first conduit to flow through the connector cavity to the second fluid conduit. A first calibration sphere is positioned relative to the connector for reflecting an ultrasonic pulse signal transmitted by the ultrasonic transducer. The reflected ultrasonic pulse signal is useable by the calibration circuitry to calibrate the ultrasonic pulse echo apparatus.

27 Claims, 5 Drawing Sheets

Acquisition Depth = $\dfrac{a}{\cos \Theta}$ + c

METHOD AND APPARATUS FOR CALIBRATING AN ULTRASONIC SENSING SYSTEM USED TO DETECT MOVING OBJECTS

RELATED APPLICATION

This application claims the priority and benefit of U.S. Provisional patent application 60/852,431, filed Oct. 18, 2006, which is incorporated herein by reference in its entirety.

TECHNICAL FIELD

The technical field relates to detecting and/or characterizing moving objects using ultrasound technology. One non-limiting application is in detecting and/or characterizing emboli in the bloodstream.

BACKGROUND

Embolic particles carried by the bloodstream can cause strokes and other circulatory disorders. During surgery, emboli may occur when clots form in the blood, air enters into the bloodstream, or tissue fragments break loose or become dislodged. The blood carries the emboli into increasingly smaller arteries until they become lodged and obstruct the flow of blood. The amount of damage that results depends on the size of the emboli, the point in which it lodges in the blood flow, the amount of blood leaking around the emboli, and how blood is supplied by collateral paths around the obstruction. The resulting functional deficit depends in part on the composition of the emboli. For example, air may be reabsorbed in a short time, clots may dissolve, (particularly if blood-thinning drugs are present), while particles composed of plaque and body tissue may not dissolve at all. Therefore, it is important to have non-invasive instrumentation that can accurately detect the presence of emboli, determine their composition, and estimate their size so that appropriate medical management decisions can be made.

Instrumentation for detecting and classifying emboli based on broadband ultrasound is described in U.S. Pat. No. 5,441,051, the disclosure of which is incorporated here by reference, and in U.S. patent application Ser. No. 11/429,432, filed on May 8, 2006, the disclosure of which is also incorporated here by reference. When an emboli passes through an ultrasound beam, the change in acoustic reflectivity causes a reflection which can be detected by an ultrasound receiver. The number of embolic events can be counted by monitoring the number of reflected echoes that exceed a predetermined threshold. An embolus may be characterized by composition and size in order to classify it for example as a gas or a fat particle based on detailed analysis of the echo signal for each embolus.

Ultrasonic echoes reflected from a moving object are typically processed in order to remove reflections from stationary objects that are of less interest, enhance signal to noise ratio, and reduce false object detections. But the accuracy of the detection and characterization of a moving object based on ultrasonic echo signal processing apparatus depends on how well that apparatus is calibrated. It is known to use "phantoms" to calibrate ultrasonic echo signal processing apparatus. Phantoms are test objects that closely mimic the ultrasonic propagative/reflective characteristics of certain materials to be analyzed such as human tissue, food products, fluids, etc. Phantom test objects typically have well known ultrasonic propagation and/or reflection characteristics. If there is a difference between determined characteristics of reflected signals from phantom objects provided by the ultrasonic echo signal processing apparatus and the well known characteristics, then the ultrasonic echo signal processing apparatus may be adjusted or calibrated to reduce that difference. One or more apparatus parameters may be adjusted such as power level/gain, frequency, phase, etc.

While phantom-based calibration methods may be effective in certain applications, such as phased-array scanners used for imaging tissue structures, the measurement of physical quantities such as the size and composition of emboli flowing through a tube of a heart-lung machine requires a higher degree of precision. For example, phantom-based calibrations are typically performed infrequently and off-line. But this is a problem for applications like blood circuit monitors, where emboli in the blood stream must often be detected on a continuous basis while in use, counted, and classified with high accuracy and speed. For example, the assignee of this application offers an EDAC™ quantifier device that detects individual micro-emboli at rates over 1000 per second, identifies micro-emboli from below 10 microns to up to 1000 microns, and instantly reports relevant data to the user. Accuracy is very important, and as a result, calibration should be performed regularly—continuously would be best, and if possible, calibration should be performed on-line and automatically.

Another issue relates to the shape of the reference object used for calibration. Although different shapes may be used, some shapes require extensive and careful alignment in order for the calibration results to be accurate. In some instances, special alignment procedures and adjustments may be necessary when orienting the reference object for calibration. This kind of precision handling is undesirable in many applications, in particular those where calibration accuracy is critical and/or where the skill set of the user may not include knowledge of proper reference object alignment/orientation.

SUMMARY

A calibration device is described for use in calibrating an ultrasonic pulse echo apparatus for detecting a moving object in a fluid, where the ultrasonic pulse echo apparatus includes an ultrasonic transducer and calibration circuitry. A connector has a first end for connecting with a first fluid conduit and a second end for connecting with a second fluid conduit. A cavity between the first and second ends permits the fluid containing the moving object from the first conduit to flow through the connector cavity to the second fluid conduit. A first calibration sphere is positioned relative to the connector for reflecting an ultrasonic pulse signal transmitted by the ultrasonic transducer. The reflected ultrasonic pulse signal is useable by the calibration circuitry to calibrate the ultrasonic pulse echo apparatus.

The first calibration sphere may be positioned on or near an outer surface of the connector in a location opposite the ultrasonic transducer used to transmit the ultrasonic pulse signal. In one non-limiting example embodiment, the connector includes a base for positioning the first calibration sphere on or near an outer surface of the connector. The base can be integral with the connector or mounted on the connector. Other positioning apparatus may be used. Although less desirable, the first calibration sphere could be positioned on or near an inner surface of the connector in a location opposite the ultrasonic transducer used to transmit the ultrasonic pulse signal.

In other non-limiting example embodiments, one or both of the first and second ends of the connector may be tapered. Alternatively, one or both of the first and second ends of the connector may be ridged. A recess may be formed in the outer surface of the connector opposite the first calibration sphere for receiving and orienting the ultrasonic transducer. A second calibration sphere may also be positioned relative to the connector and adjacent to the first calibration sphere for reflecting an ultrasonic pulse signal transmitted by the ultrasonic transducer. In that case, at least one of the ultrasonic pulse signals reflected by the first and second calibration spheres is useable by the calibration circuitry to calibrate the ultrasonic pulse echo apparatus. When the transducer is inserted in a first orientation in the recess, one of the first and second calibration spheres is useable by the calibration circuitry to calibrate the ultrasonic pulse echo apparatus. Alternatively, when the transducer is inserted in a second orientation in the recess, one of the first and second calibration spheres is useable by the calibration circuitry to calibrate the ultrasonic pulse echo apparatus.

A calibration system is also described for calibrating an ultrasonic pulse echo apparatus for detecting a moving object in a fluid using the connector and calibration sphere. The ultrasonic pulse echo apparatus includes an ultrasonic transducer for transmitting an ultrasonic pulse signal in a direction that intersects a path of the moving object and receiving an echo signal from an object in a field of view of the ultrasonic pulse signal and processing circuitry for processing the echo signal including calibration circuitry for calibrating echo signal processing. The connector is positioned to intersect with the field of view of the ultrasonic pulse signal and has a first end for connection with a first fluid conduit and a second end for connection with a second fluid conduit. The connector further includes a cavity between the first and second ends to permit the fluid containing the moving object from the first conduit to flow through the connector cavity to the second fluid conduit. A first calibration sphere is positioned relative to the connector and in the field of view of the ultrasonic pulse signal for reflecting the ultrasonic pulse signal transmitted by the ultrasonic transducer.

The calibration circuitry is configured to calibrate the echo signal processing using the reflected ultrasonic pulse signal. The calibration circuitry is configured to determine a difference between a magnitude of the reflected ultrasonic pulse signal and a predetermined value and to adjust the echo signal processing to reduce the difference. As a safeguard, the calibration circuitry may also be configured to determine whether the difference is within a predetermined range before adjusting the echo signal.

In one non-limiting example embodiment, the ultrasonic pulse signal includes a series of broadband pulses transmitted at a frequency on order of several MHz. As described above, a second calibration sphere may be positioned relative to the connector and adjacent to the first calibration sphere for reflecting an ultrasonic pulse signal transmitted by the ultrasonic transducer. One of the ultrasonic pulse signals reflected by the first and second calibration spheres is useable by the calibration circuitry to calibrate the echo signal processing.

In one non-limiting, example application, the fluid includes blood, and the ultrasonic pulse echo apparatus is configured to monitor objects in the blood. But regardless of the type of fluid being monitored, the calibration circuitry is configured to calibrate the echo signal processing using the reflected ultrasonic pulse signal while also monitoring the fluid for moving objects.

A method for calibrating an ultrasonic pulse echo apparatus for detecting a moving object in a fluid is also described and includes the following steps:

transmitting an ultrasonic pulse signal in a direction that intersects a path of the moving object;

positioning a connector to intersect with the field of view of the ultrasonic pulse signal;

positioning a first calibration sphere relative to the connector and in the field of view of the ultrasonic pulse signal, the first calibration sphere reflecting the ultrasonic pulse signal transmitted by the ultrasonic transducer, receiving the reflected ultrasonic pulse signal; and calibrating ultrasonic pulse echo apparatus using the reflected ultrasonic pulse signal.

As described above, the calibrating may include determining a difference between a magnitude of the reflected ultrasonic pulse signal and a predetermined value and to adjust the echo signal processing to reduce the difference. The difference may also be checked to see if it is within a predetermined range before adjusting the echo signal. And the ultrasonic pulse signal may be transmitted as a series of broadband pulses at a frequency on order of several MHz.

The method may also include receiving and orienting the ultrasonic transducer in a recess formed in the outer surface of the connector opposite the first calibration sphere, positioning a second calibration sphere relative to the connector and adjacent to the first calibration sphere for reflecting an ultrasonic pulse signal transmitted by the ultrasonic transducer, and using at least one of the ultrasonic pulse signals reflected by the first and second calibration spheres to calibrate the ultrasonic pulse echo apparatus.

DETAILED DESCRIPTION

In the following description, for purposes of explanation and non-limitation, specific details are set forth in order to provide an understanding of the described technology. It will be apparent to one skilled in the art that other embodiments may be practiced apart from the specific details disclosed below. In other instances, detailed descriptions of well-known methods, devices, techniques, etc. are omitted so as not to obscure the description with unnecessary detail. Individual function blocks are shown in the figures. Those skilled in the art will appreciate that the functions of those blocks may be implemented using individual hardware circuits, using software programs and data in conjunction with a suitably programmed microprocessor or general purpose computer, using applications specific integrated circuitry (ASIC), field programmable gate arrays, one or more digital signal processors (DSPs), etc.

Figure 1:
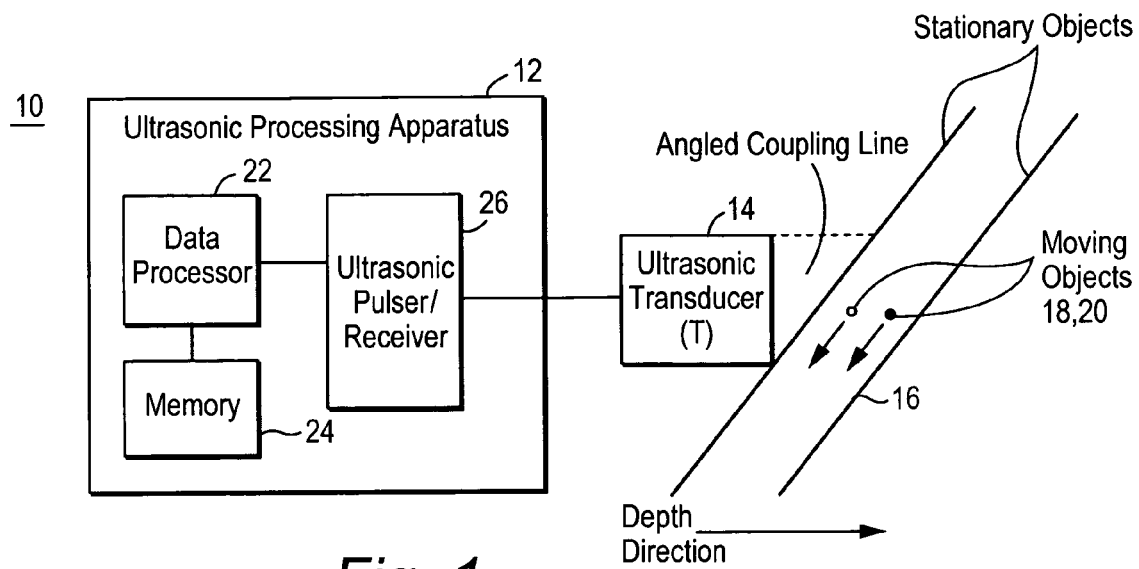
FIG. 1 is a function block diagram illustrating one non-limiting example of an ultrasonic detection apparatus.

FIG. 1 shows a non-limiting example embodiment of a moving object detection system which is indicated by the numeral 10. For purposes of explanation only, and not limitation, the moving object detection apparatus 10 is sometimes described in the context of an emboli detection application. Of course, this technology may be used with other applications. Several other example applications include mechanically scanning structures, parts, or other apparatus for defects, scanning any type of fluid for particles, free hand ultrasound applications, or preferentially enhancing signals from moving fluid through a stationary background.

The moving object detection system 10 includes an ultrasonic processing apparatus 12 that controls an ultrasound transducer 14 positioned so that as moving objects 18 and 20 pass by the ultrasound transducer 14, ultrasonic pulses impinge on the moving objects resulting in reflected echoes that are detected by the ultrasound transducer 14. Stationary objects 16, shown as a tube or vessel with close and far walls, are also insonified by the ultrasonic pulses and also produce reflected echoes which are detected by the ultrasound transducer 14. In an emboli detection application, the stationary objects correspond to blood vessel walls or walls of other blood transport conduit, and the moving objects correspond to emboli. The term "depth" corresponds to the perpendicular direction away from the ultrasound transducer 14 towards the objects. The ultrasonic processing apparatus includes a data processor 22 coupled to memory 24 and to an ultrasonic pulser/receiver 26.

The ultrasound transducer 14 transmits ultrasound pulses into the body and receives echoes or reflections from within the body. As one non-limiting example, the transducer 14 may be a PZT composite having a quarter wave impedance matching layer to increase the coupling of sound from the transducer 14 into the object objects. The ultrasonic pulser 26 also preferably (but not necessarily) applies fast rise-time step electrical pulses to the transducer 14 which are converted by the transducer 14 into fast rise-time step ultrasound signals that reflect off the objects being scanned. The fast rise-time step pulses are broadband signals, which are advantageous in blood monitor and other moving object detection applications because the provide better spatial resolution for tracking and classifying individual micro-emboli. One non-limiting, example drive pulse has a voltage over 100 volts and a rise time on the order of 15 nanoseconds. As one non-limiting example, the broadband pulses may be generated at a frequency on the order of several MHz. Of course, other frequencies may be used depending on the application. The inventors determined that using broadband pulses requires a special connector to ensure that sufficient energy is transmitted into the flow to obtain a strong reflection in order to detect very small micro-emboli (e.g., around 10 microns).

Reflections or echoes from the acoustic impedance changes in the body return to the transducer 14 which converts the reflected acoustic energy into corresponding electronic echo signals. The transducer 14 preferably has a broad bandwidth so that, among other things, it can preserve the polarity of the reflected signals. A plurality of ultrasound transducers may be arranged in an array and operated sequentially to produce adjacent beams that collectively cover larger areas.

Figure 2:
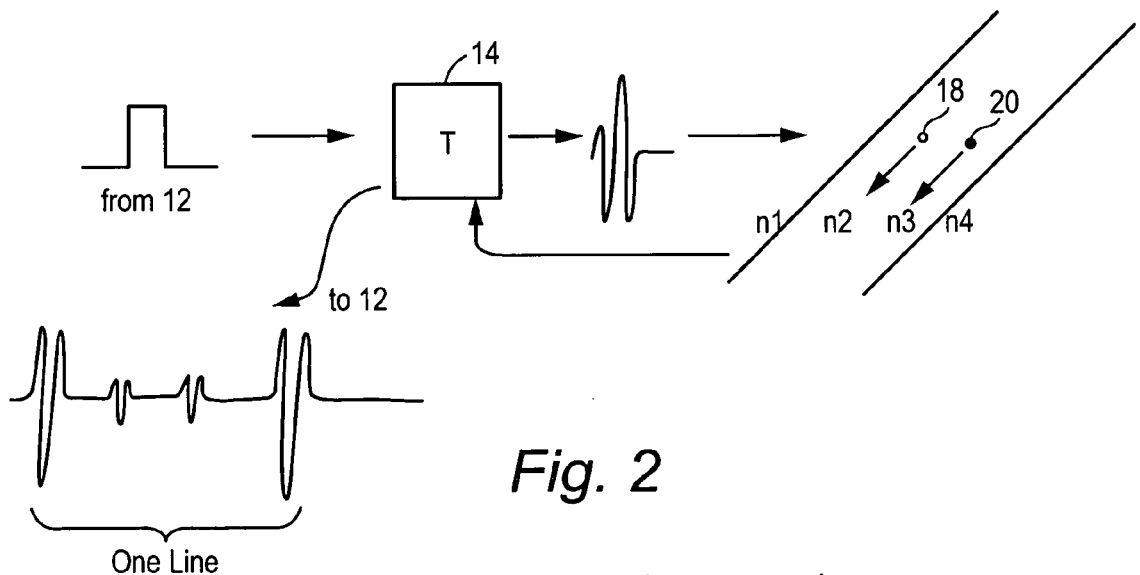
FIG. 2 illustrates an ultrasonic pulse being reflected as RF echoes by stationary and moving objects.

FIG. 2 is a simplified conceptual drawing that illustrates the pulse from the ultrasonic pulser 26 energizing the ultrasonic transducer 14 to generate an ultrasonic quasi-sinusoidal looking wave that impinges on the stationary walls 16 and the moving objects 18 and 20. For each pulse or "ping", each moving and stationary object produces one or more RF echoes. RF echo 1 corresponds to the stationary front wall 16; RF echo 2 corresponds to the moving object 18; RF echo 3 corresponds to the moving object 20; and RF echo 4 corresponds to the stationary back wall 16. All of the echoes that result from one ultrasonic pulse or "ping" are combined together as a single "line". Multiple lines are then preferably processed as described in the commonly-assigned U.S. patent application Ser. No. 11/429,432.

Figure 3:
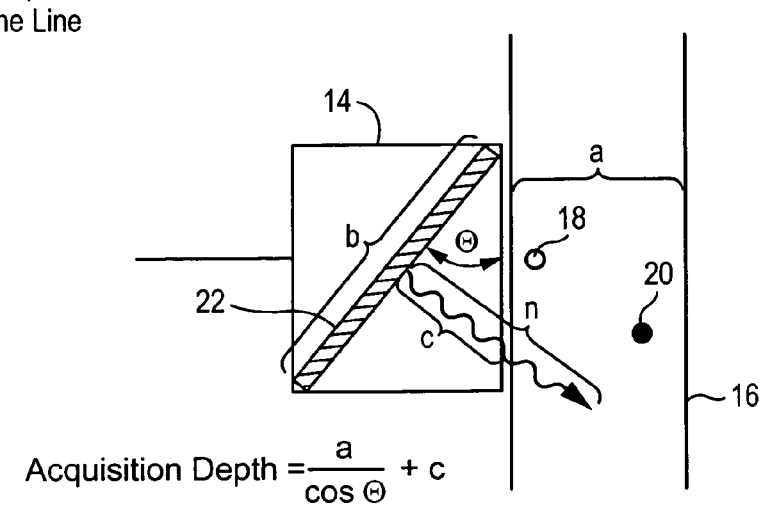
FIG. 3 illustrates the ultrasonic transducer positioned at an angle with respect to the direction of movement of the moving objects and related parameters.

The ultrasound beam is preferably angled with respect to the moving object direction, e.g., the blood flow direction for emboli, so that the effective range from the transducer face to the moving object changes as the moving object passes through the sound beam. This change in the range with respect to time produces a moving object indicator (MOI) shift. FIG. 3 illustrates that angle θ, which may have any suitable value. One non-limiting example value is 30 degrees. Angling the beam makes the moving object shift much larger than that of the surrounding stationary objects, so that the moving object indicator can more easily separate and cancel the echoes from the stationary objects. In addition, an angled beam reduces the strength of echoes from the stationary walls so that dynamic range requirements for detection and signal processing are reduced. The width of the transducer is designated as "b", the width of the tube or blood vessel is "a", and the range "n" is in a direction perpendicular to the surface of the transducer towards the tube or vessel. The range distance from the tube wall to the external surface of the transducer is denoted as "c". The ultrasonic processing apparatus is set to acquire echo lines at a maximum acquisition depth equal to the distance from the transducer face to the back wall of the tube, which equals a/cos θ+c. The distance "c" from the transducer tube wall is shortest at the top of the transducer and longest at the bottom, angled away from the transducer, so that echoes from the tube wall will be spread out over multiple range values n.

The ultrasonic receiver 26 amplifies the small electrical echoes from the transducer 14 to a level suitable for analyzing and processing. The receiver includes amplification, time gain compensation, filtering, and analog-to-digital conversion. Time gain compensation increases gain with time to compensate for the acoustic attenuation experienced as the ultrasound pulse travels deeper in the depth direction shown in FIG. 1. Analog-to-digital conversion needs to take place at a rate high enough to preserve the characteristics of the reflected echo signals from the moving objects. As one non-limiting example, with an ultrasound signal centered at 5 MHz, analog-to-digital (A-to-D) conversion rates should be 20 MHz or higher. The A-to-D converter preferably has sufficient accuracy to preserve amplitude and polarity information.

The digitized echo outputs are passed to the data processor 22 for subsequent signal processing and stored in the memory 24. The data processor 22 analyzes the electronic echo signals to detect and preferably classify each moving object based on size and composition. If desired, the results of the moving object detection and classification may be displayed or used to produce audible tones, alarms, pre-recorded voice messages, or other signals.

Figure 4:
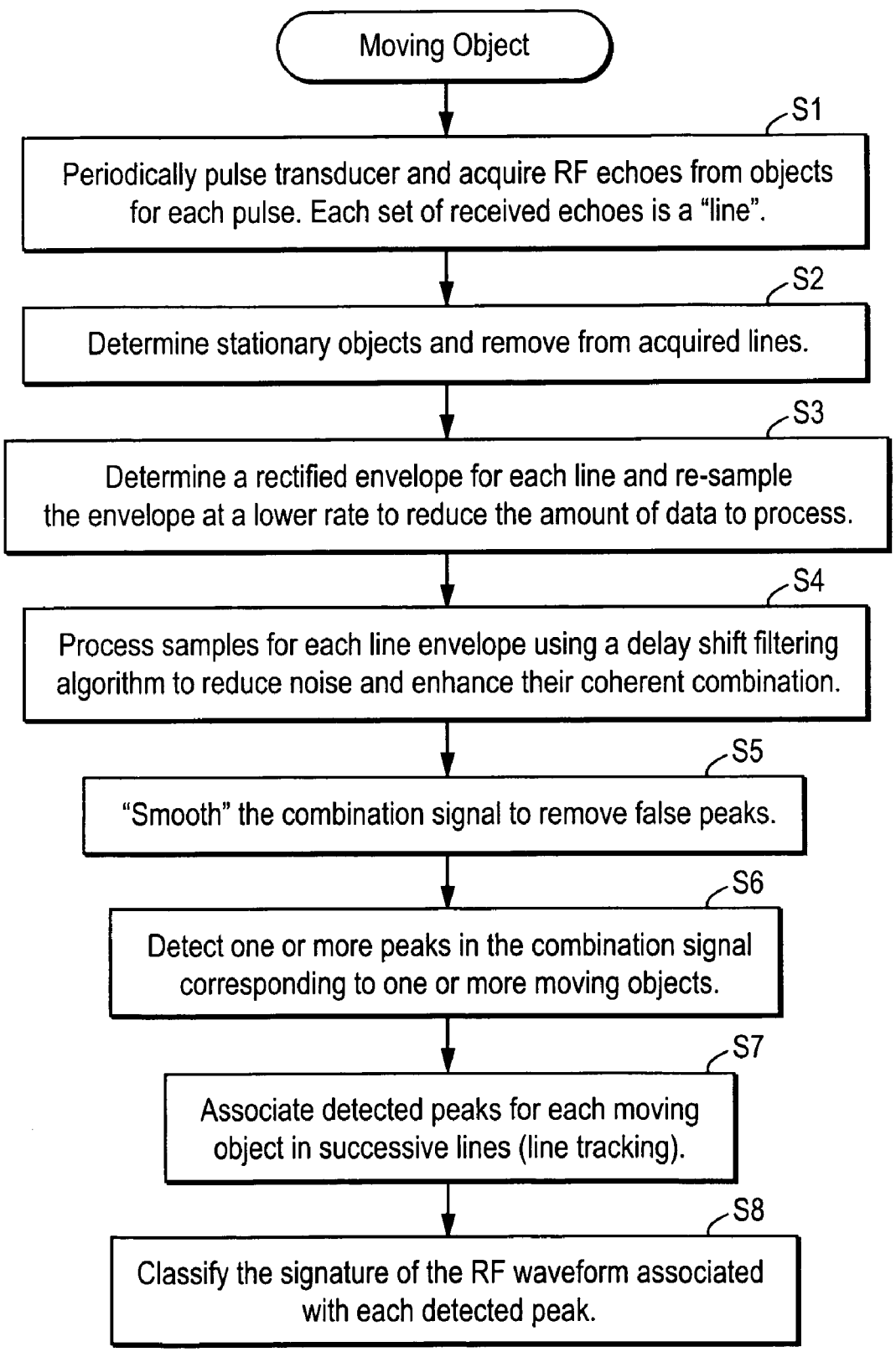
FIG. 4 is a flowchart labeled "moving object" that outlines non-limiting, example signal processing procedures that may be performed on digitized echo signals.

FIG. 4 illustrates a flowchart labeled "moving object" that outlines non-limiting, example signal processing procedures that may be performed on digitized echo signals in accordance with the teachings in commonly-assigned U.S. patent application Ser. No. 11/429,432. But the calibration device, apparatus, and method described here may be used to calibrate any ultrasonic moving object detector and is expressly not limited to the details shown in FIG. 4 and now described.

In step S1, the ultrasonic transducer is periodically pulsed to acquire RF echoes from both stationary and moving objects for each pulse. Each set of received echoes per pulse is referred to as a line. The echoes from stationary objects in each line are determined and removed (step S2). A rectified envelope is then determined for each line, and the rectified envelope is re-sampled at a lower sampling rate to reduce the amount of data needed to be processed (step S3). The samples for each line envelope are then processed using a delay shift filtering algorithm to reduce noise and to enhance the coherent combination of multiple envelope lines (step S4). To further improve the inherent line combination process, a further filtering operation is performed to "smooth" the combined signal to remove false peaks (step S5). Then, in step S6, one or more peaks (depending on a number of moving objects) are detected in the combination signal, with each peak detected corresponding to a moving object. The detected peaks in successive lines that corresponds to the same moving object are associated in a process called "line tracking" (step S7). This line tracking, as described below, allows prediction of the future position (range) and velocity of the moving object which allows subsequent analyzing and processing to be focused on a narrower region in terms of position and velocity by excluding all other positions and velocities. The last step describes classifying the "signature" or characteristics of the RF wave form associated with each detected peak (step S8). In some applications, such as emboli detection, classification of the moving object can be very important. For example, the polarity or the phase of the echo may be used to classify an embolus as either gaseous or solid.

Figure 5:
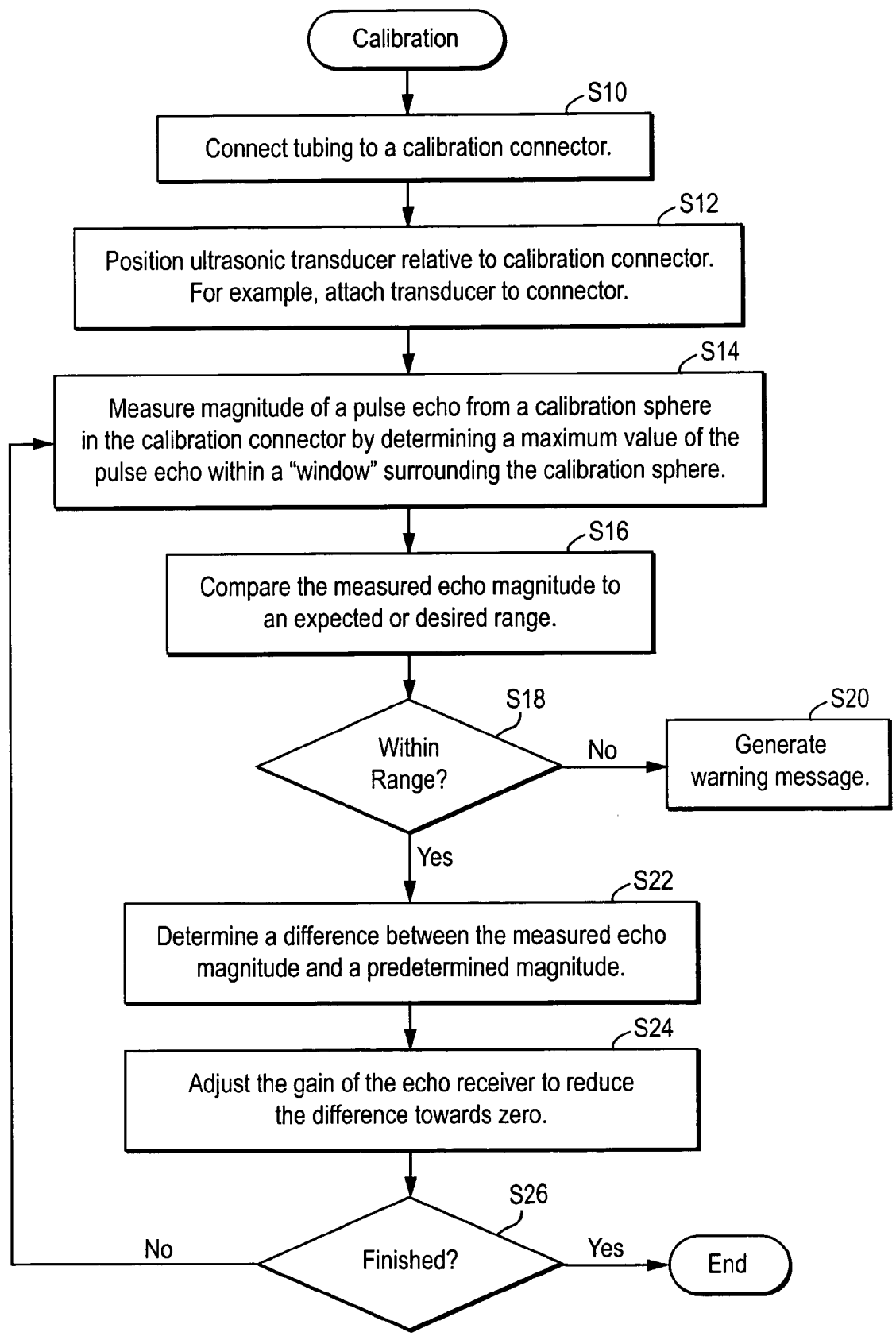
FIG. 5 is a flow chart diagram illustrating non-limiting example steps for calibrating an ultrasonic detection apparatus used to detect and/or classify moving objects.

FIG. 5 illustrates a flowchart labeled "Calibration" that illustrates example, non-limiting procedures for calibrating an ultrasonic moving object detector. First, an in-line calibration connector (non-limiting examples of which are described below) is connected to the conduit that conveys the fluid to be monitored for moving objects in the fluid (step S10). An ultrasonic transducer is then positioned relative to the in-line calibration connector (step S12). Although that positioning may occur in any number of ways, in examples described below, the transducer is attached to or mounted on the connector. But the transducer does not need to be attached or mounted on the connector.

The ultrasonic transducer is operated as usual, and the magnitude of a pulse echo from a calibration sphere provided in or adjacent to the calibration connector is determined from a maximum value of the pulse echo within a positional window surrounding the calibration sphere's location (step S14). As one non-limiting example, the window may start 0.1 cm before the known depth of the calibration sphere (having a non-limiting example diameter of about 3 mm) and end 0.1 cm after that known position. The measured echo magnitude is compared to an expected or desired range (step S16), and a decision is made whether the measured echo magnitude is within that range (step S18). If not, a warning message is generated (step S20). For example, the transducer may not have been positioned properly, so a message might be displayed to a user to re-orient, re-attach, re-insert, or re-position the transducer relative to the calibration connector. If desired, specific instructions could also be provided to the user explaining how to re-orient, re-attach, re-insert, or re-position the transducer relative to the calibration connector.

If the measured echo magnitude is within range, a difference is determined between the measured echo magnitude and a predetermined magnitude (step S22). The gain of the echo receiver 26 or other echo processing parameter may adjusted by the data processor 22 to reduce the difference towards zero (step S24). A decision is made in step S26 whether the calibration is finished. If not, the procedures are repeated starting from step S14.

Figure 6:
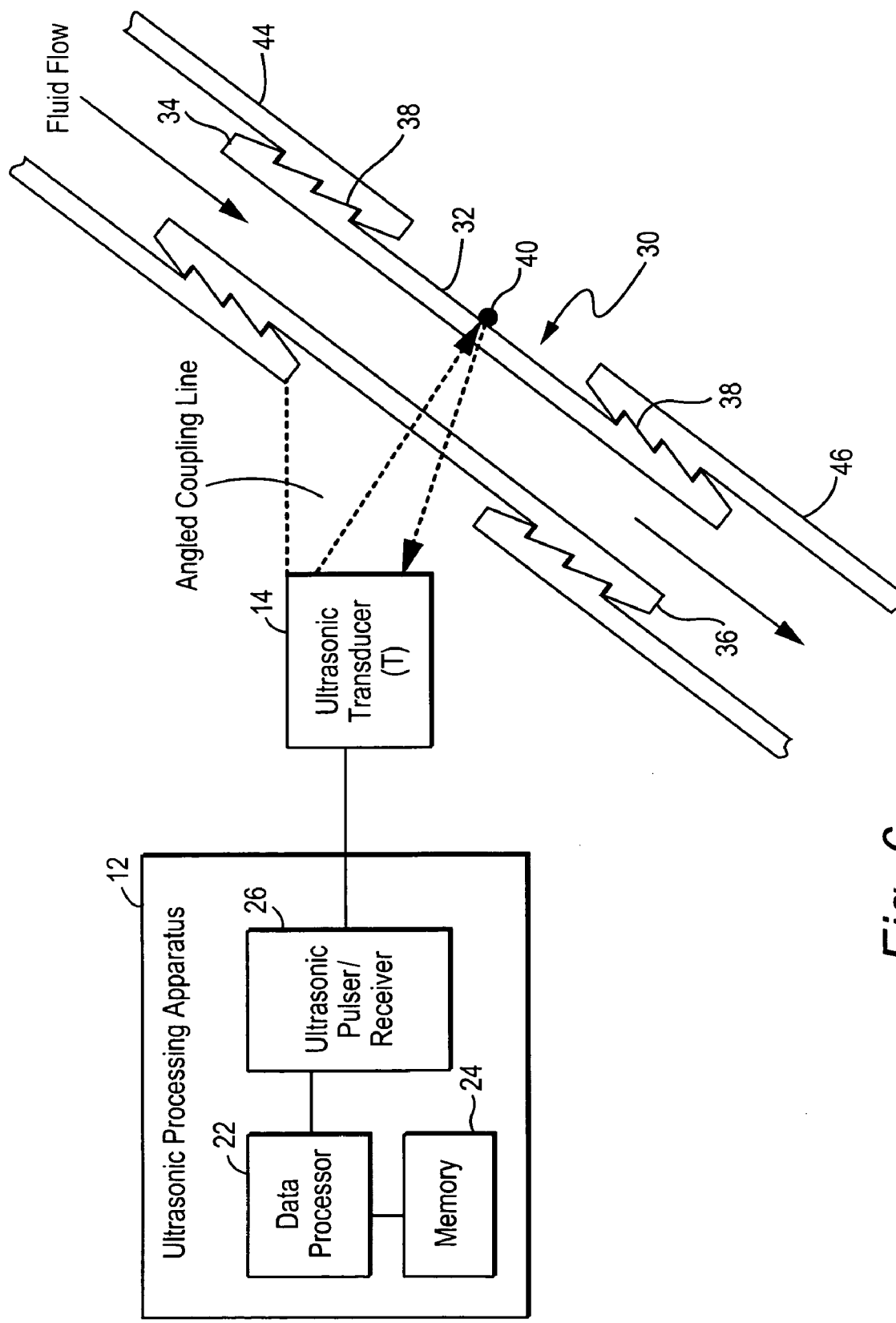
FIG. 6 is a diagram illustrating a non-limiting example of an ultrasonic detection apparatus with a calibrating connector.

FIG. 6 illustrates one non-limiting example embodiment of an in-line calibration connector 30 for use with the non-limiting example ultrasonic processing system 10 shown in FIG. 1. The in-line calibration connector provides more control over the measurement geometry and acoustic transmission properties than alternative systems in which the ultrasound sensors are clamped over existing tubing. As a result, ultrasonic measurement systems that employ the in-line calibration connector can provide better measurement sensitivity and repeatability. The ultrasonic transducer 14 directs broadband ultrasound signals into the connector, preferably but not necessarily at an angle, and receives echoes from emboli (or other objects) moving through the connector 30. The connector 30 includes a body 32 with two ends 34 and 36 that are preferably (but not necessarily) shaped to be integrated with/connect to first and second fluid conduits 44 and 46, respectively. The fluid flows from the first conduit 44 through the connector 30 into the second conduit 46. Non-limiting example fluid conduits in the blood monitoring application typically include clear PVC, other plastic, or rubber tubing. Any type of fluid conduit may be used, and any suitable coupling may be used to couple the ends of the conduits and the connector. For example, if the fluid conduits are flexible, the ends of the connector may optionally be tapered and/or ridged to facilitate connection, adhesion, and sealing. Different taper or ridged profiles may be used. FIG. 6 shows a non-limiting example of ridges 38 formed on the outer surfaces near the two connector ends to facilitate coupling the connector 30 with the first and second conduits 44 and 46.

A calibration sphere 40 is positioned relative to the ultrasonic transducer 14 to reflect a broadband ultrasonic pulse for detection by the ultrasonic transducer 14. Preferably, the calibration sphere 40 is positioned opposite the ultrasonic transducer 14. Advantageously, because the calibration sphere 40 is round, its positioning and orientation relative to the ultrasonic transducer 14 are not critical. In contrast, if a calibration plate were used, then the plate would have to be precisely positioned opposite the ultrasonic transducer 14 and oriented perpendicularly in order for calibration to be accurate. As a result, angular adjustments would normally be necessary with such a calibration plate to achieve the proper calibration position and orientation.

The calibration sphere 40 is preferably made of or includes a material that provides a high ultrasonic echo contrast such as metal or a hollow gas-filled space. One non-limiting example of a gas is air. But other materials or composite materials may be used. Also preferably but not necessarily, the surface of the calibration sphere 40 is smooth, clean, and free of defects and discontinuities. The connector 30 may be composed of any suitable material(s). For example, polycarbonate may be preferred from a regulatory standpoint. But if alternate materials can be used without raising biocompatibility or other concerns, materials with less acoustic attenuation than polycarbonate may be preferred such as: acrylic, polystyrene, polyethylene, and polypropylene.

The calibration sphere 40 may be affixed to, mounted on, or positioned relative to the connector 30. FIG. 6 shows the calibration sphere 40 located on an outer surface of the connector 40 opposite the transducer 14. It may be preferable in some applications that the calibration sphere 40 not come in contact with the fluid or impede the fluid flow. It is also preferable that the calibration sphere 40 be positioned in a location so that the same echo signature is obtained regardless of angle of the transducer beam.

Figure 7:
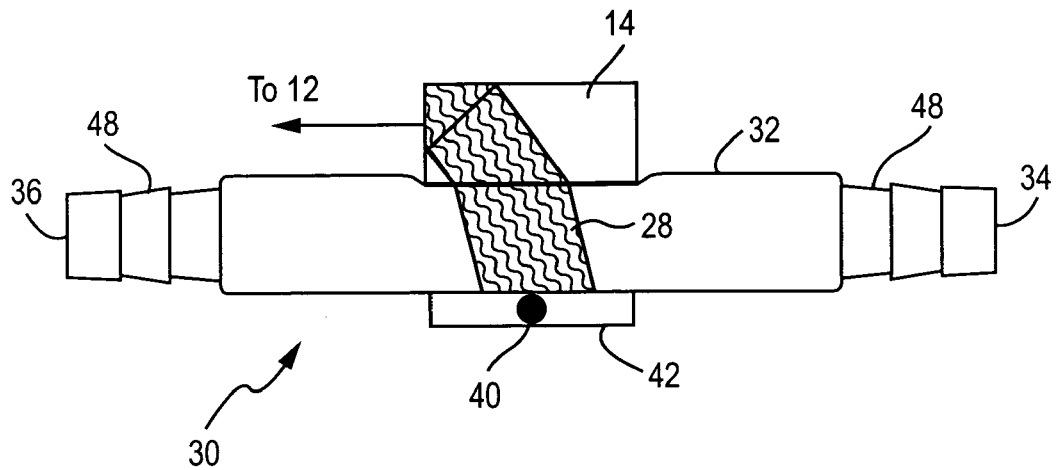
FIG. 7 is a diagram illustrating a non-limiting example of a calibrating connector including one sphere.

In view of these considerations, another non-limiting example embodiment of the connector 30 is shown in FIG. 7 with a base 42 for holding the calibration sphere 40 in a location that does not impede fluid flow through the connector 30 or exposes the calibration sphere 40 to contact with the fluid. The base 42 may, for example, be integral with the opposing wall of the connector 30 so that there is no ultrasonic scattering from connector/base interface. But other methods for mounting or positioning calibration sphere 40 relative to the connector 30 may be used. By fixing the position of the calibration sphere 40 in the base 42 ensures that the sphere receives and consistently reflects an echo from the broadband ultrasonic signal 28 generated by the ultrasonic transducer 14. The base can be a substantially solid region with the calibration sphere held in place by the surrounding solid material or a region with some hollows with the calibration sphere affixed in the desired position by adhesive or other method. FIG. 7 also shows a non-limiting example where the ends 34 and 36 are tapered as indicated generally at 48.

Figure 8A:
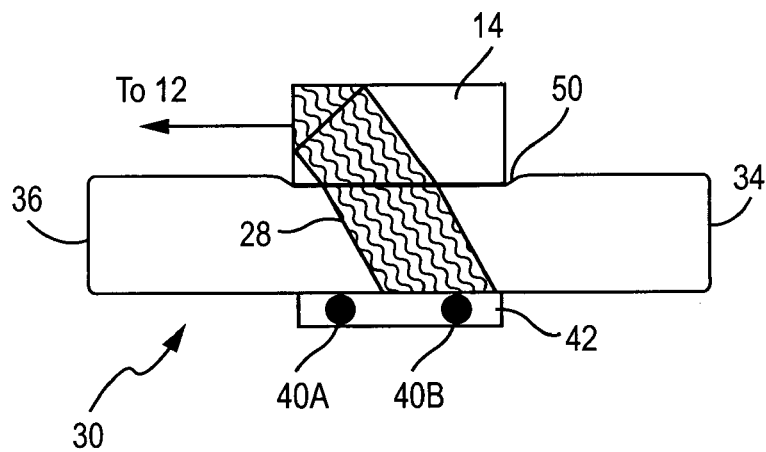
FIG. 8A is a diagram illustrating a non-limiting example of a calibrating connector including two spheres with the ultrasonic transducer mounted in one configuration.
Figure 8B:
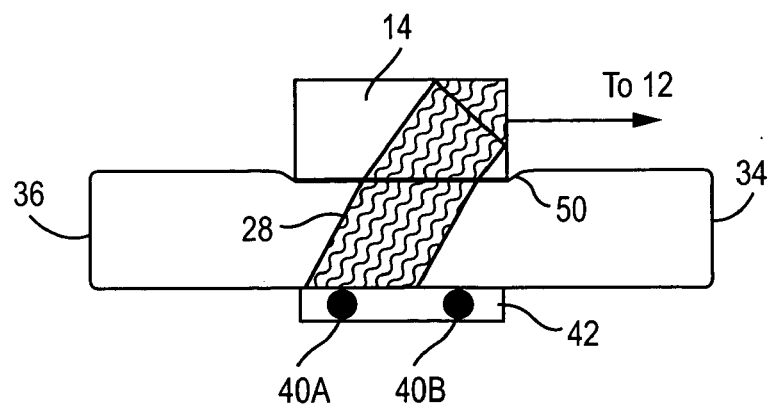
FIG. 8B is a diagram illustrating a non-limiting example of a calibrating connector including two spheres with the ultrasonic transducer mounted in an opposite configuration.

Although a single calibration sphere 40 may be used, other non-limiting example embodiments may use two or more calibration spheres 40. Indeed, it may be advantageous to use two or more calibration spheres 40 when the ultrasonic transducer 14 can be positioned in two or more positions or orientations such that the ultrasonic signal 28 generated by the ultrasonic transducer 14 may be directed to different areas. FIGS. 8A and 8B show a non-limiting example of a connector having a recess 50 for receiving and holding in position the ultrasonic transducer 14. The transducer may be further secured using for example tape, a clamp, a wrap, an elastic band, etc., but such additional security is optional.

Although the recess may be "keyed" so that the ultrasonic transducer 14 may only be inserted in one orientation, the recess 50 may be shaped so that the ultrasonic transducer 14 may be fitted in the recess 50 in a first orientation, such as that shown in FIG. 8A, or in a second orientation, such a that shown in FIG. 8B. In the latter situation, having two calibration spheres 40A and 40B positioned, for example in the base 42, so that the ultrasonic signal 28 sufficiently impinges on at least one of the spheres. In the first orientation, the ultrasonic signal 28 impinges on the calibration sphere 40B, and in the second orientation, the ultrasonic signal 28 impinges on the calibration sphere 40A. In either orientation, the same echo signature is obtained.

The in-line connector described here provides uniform transmission and reception of broadband ultrasonic signals used to detect, track, size and classify moving particles in fluid. The scattering sphere located in the bottom of the connector provides a reference echo that can account for small variations in echo amplitude due to manufacturing variations in detector sensitivity, variations in coupling energy between the connector and the detector, and variations in transmission due to probe placement. The in-line connector reduces these variations by providing a more uniform measurement geometry and improved acoustic transmission into the connector.

Although various embodiments have been shown and described in detail, the claims are not limited to any particular embodiment or example. None of the above description should be read as implying that any particular element, step, range, or function is essential such that it must be included in the claims scope. Reference to an element in the singular is not intended to mean "one and only one" unless explicitly so stated, but rather "one or more." The scope of patented subject matter is defined only by the claims. The extent of legal protection is defined by the words recited in the allowed claims and their equivalents. All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. No claim is intended to invoke paragraph 6 of 35 USC §112 unless the words "means for" or "step for" are used. Furthermore, no feature, component, or step in the present disclosure is intended to be dedicated to the public regardless of whether the feature, component, or step is explicitly recited in the claims.

The invention claimed is:

1. A calibration device for use in calibrating ultrasonic pulse echo apparatus for detecting a moving object in a fluid, where the ultrasonic pulse echo apparatus includes an ultrasonic transducer and calibration circuitry, the calibration device comprising:

a connector for connecting at a first end with a first fluid conduit and at a second end with a second fluid conduit, the connector including a cavity between the first and second ends to permit the fluid containing the moving object from the first conduit to flow through the connector cavity to the second fluid conduit, and a first calibration sphere positioned relative to the connector for reflecting an ultrasonic pulse signal transmitted by the ultrasonic transducer, wherein the reflected ultrasonic pulse signal is useable by the calibration circuitry to calibrate the ultrasonic pulse echo apparatus, and wherein the connector further comprises a recess formed in the outer surface of the connector opposite the first calibration sphere for receiving and orienting the ultrasonic transducer.

2. The calibration device in claim 1, wherein the first calibration sphere is positioned on or near an outer surface of the connector in a location opposite the ultrasonic transducer used to transmit the ultrasonic pulse signal.

3. The calibration device in claim 2, wherein the connector includes a base for positioning the first calibration sphere on or near the outer surface of the connector.

4. The calibration device in claim 3, wherein the base is integral with the connector.

5. The calibration device in claim 3, wherein the base is mounted on the connector.

6. The calibration device in claim 1, wherein the first calibration sphere is positioned on or near an inner surface of the connector in a location opposite the ultrasonic transducer used to transmit the ultrasonic pulse signal.

7. The calibration device in claim 1, wherein one or both of the first and second ends of the connector are tapered.

8. The calibration device in claim 1, wherein one or both of the first and second ends of the connector are ridged.

9. The calibration device in claim 1, further comprising a second calibration sphere positioned relative to the connector and adjacent to the first calibration sphere for reflecting an ultrasonic pulse signal transmitted by the ultrasonic transducer, wherein at least one of the ultrasonic pulse signals reflected by the first and second calibration spheres is useable by the calibration circuitry to calibrate the ultrasonic pulse echo apparatus.

10. The calibration device in claim 9, wherein when the transducer is inserted in a first orientation in the recess, the calibration circuitry is configured to use one of the first and second calibration spheres to calibrate the ultrasonic pulse echo apparatus, and when the transducer is inserted in a second orientation in the recess, the calibration circuitry is configured to use one of the first and second calibration spheres to calibrate the ultrasonic pulse echo apparatus.

11. A calibration system, comprising:
an ultrasonic pulse echo apparatus for detecting a moving object in a fluid including:
an ultrasonic transducer for transmitting an ultrasonic pulse signal in a direction that intersects a path of the moving object and receiving an echo signal from an object in a field of view of the ultrasonic pulse signal; and
processing circuitry for processing the echo signal including calibration circuitry for calibrating echo signal processing;
a connector positioned to intersect with the field of view of the ultrasonic pulse signal having a first end for connection with a first fluid conduit and a second end for connection with a second fluid conduit, the connector further including a cavity between the first and second ends to permit the fluid containing the moving object from the first conduit to flow through the connector cavity to the second fluid conduit; and
a first calibration sphere positioned relative to the connector and in the field of view of the ultrasonic pulse signal for reflecting the ultrasonic pulse signal transmitted by the ultrasonic transducer,
wherein the calibration circuitry is configured to calibrate the echo signal processing using the reflected ultrasonic pulse signal while also monitoring the fluid for moving objects.

12. The calibration system in claim 11, wherein the ultrasonic pulse signal includes a series of broadband pulses transmitted at a frequency on order of several MHz.

13. The calibration system in claim 11, wherein the connector includes a base for positioning the first calibration sphere on or near the outer surface of the connector.

14. The calibration system in claim 11, wherein the connector further comprises a recess formed in the outer surface of the connector opposite the first calibration sphere for receiving and orienting the ultrasonic transducer.

15. The calibration system in claim 14, further comprising a second calibration sphere positioned relative to the connector and adjacent to the first calibration sphere for reflecting an ultrasonic pulse signal transmitted by the ultrasonic transducer,
wherein at least one of the ultrasonic pulse signals reflected from one of the first and second calibration spheres is useable by the calibration circuitry to calibrate the echo signal processing.

16. The calibration device in claim 15, wherein when the transducer is inserted in a first orientation in the recess, one of the first and second calibration spheres is useable by the calibration circuitry to calibrate the echo signal processing, and when the transducer is inserted in a second orientation in the recess, one of the first and second calibration spheres is useable by the calibration circuitry to calibrate the echo signal processing.

17. The calibration system in claim 11, wherein the fluid includes blood and the ultrasonic pulse echo apparatus is configured to monitor objects in the blood.

18. The calibration system in claim 11, wherein the calibration circuitry is configured to determine a difference between a magnitude of the reflected ultrasonic pulse signal and a predetermined value and to adjust the echo signal processing to reduce the difference.

19. The calibration system in claim 18, wherein the calibration circuitry is configured to determine whether the difference is within a predetermined range before adjusting the echo signal.

20. A method for calibrating an ultrasonic pulse echo apparatus for detecting a moving object in a fluid, comprising:
positioning a connector with one or more calibration objects to intersect with the field of view of the ultrasonic pulse signal;
transmitting an ultrasonic pulse signal in a direction that intersects a path of the moving object;
positioning a first calibration sphere relative to the connector and in the field of view of the ultrasonic pulse signal, the first calibration sphere reflecting the ultrasonic pulse signal transmitted by the ultrasonic transducer,
receiving the reflected ultrasonic pulse signal;
calibrating ultrasonic pulse echo apparatus using the reflected ultrasonic pulse signal;
connecting a first end of the connector with a first fluid conduit; and
connecting a second end of the connector with a second fluid conduit;
wherein the connector includes a cavity between the first and second ends to permit the fluid containing the moving object from the first conduit to flow through the connector cavity to the second fluid conduit.

21. The method in claim 20, further comprising determining a difference between a magnitude of the reflected ultrasonic pulse signal and a predetermined value and to adjust the echo signal processing to reduce the difference.

22. The method in claim 21, further comprising determining whether the difference is within a predetermined range before adjusting the echo signal.

23. The method in claim 20, further comprising transmitting the ultrasonic pulse signal as a series of broadband pulses at a frequency on order of several MHz.

24. A method for calibrating an ultrasonic pulse echo apparatus for detecting a moving object in a fluid, comprising:
positioning a connector with one or more calibration objects to intersect with the field of view of the ultrasonic pulse signal;
transmitting an ultrasonic pulse signal in a direction that intersects a path of the moving object;
positioning a first calibration sphere relative to the connector and in the field of view of the ultrasonic pulse signal, the first calibration sphere reflecting the ultrasonic pulse signal transmitted by the ultrasonic transducer,
receiving the reflected ultrasonic pulse signal; and
calibrating ultrasonic pulse echo apparatus using the reflected ultrasonic pulse signal, the method further comprising:
receiving and orienting the ultrasonic transducer in a recess formed in the outer surface of the connector opposite the first calibration sphere.

25. A method for calibrating an ultrasonic pulse echo apparatus for detecting a moving object in a fluid, comprising:
positioning a connector with one or more calibration objects to intersect with the field of view of the ultrasonic pulse signal;
transmitting an ultrasonic pulse signal in a direction that intersects a path of the moving object;
positioning a first calibration sphere relative to the connector and in the field of view of the ultrasonic pulse signal, the first calibration sphere reflecting the ultrasonic pulse signal transmitted by the ultrasonic transducer,
receiving the reflected ultrasonic pulse signal; and calibrating ultrasonic pulse echo apparatus using the reflected ultrasonic pulse signal, the method further comprising:
positioning a second calibration sphere relative to the connector and adjacent to the first calibration sphere for reflecting an ultrasonic pulse signal transmitted by the ultrasonic transducer, and
using at least one of the ultrasonic pulse signals reflected by the first and second calibration spheres to calibrate the ultrasonic pulse echo apparatus.

26. The method in claim 25, further comprising:
inserting the transducer in a first orientation in the recess and using one of the first and second calibration spheres to calibrate the ultrasonic pulse echo apparatus, and
inserting the transducer in a second orientation in the recess and using one of the first and second calibration spheres to calibrate the ultrasonic pulse echo apparatus.

27. A method for calibrating an ultrasonic pulse echo apparatus for detecting a moving object in a fluid, comprising:
positioning a connector with one or more calibration objects to intersect with the field of view of the ultrasonic pulse signal;
transmitting an ultrasonic pulse signal in a direction that intersects a path of the moving object;
positioning a first calibration sphere relative to the connector and in the field of view of the ultrasonic pulse signal, the first calibration sphere reflecting the ultrasonic pulse signal transmitted by the ultrasonic transducer,
receiving the reflected ultrasonic pulse signal; and
calibrating ultrasonic pulse echo apparatus using the reflected ultrasonic pulse signal, the method further comprising:
calibrating the ultrasonic pulse echo apparatus using the reflected ultrasonic pulse signal while also monitoring the fluid for moving objects.

* * * * *